US010166050B2

(12) United States Patent
Heuer

(10) Patent No.: US 10,166,050 B2
(45) Date of Patent: Jan. 1, 2019

(54) INSTRUMENT FOR CONNECTING A CORRECTION ROD TO A BONE SCREW

(71) Applicant: SILONY MEDICAL INTERNATIONAL AG, Frauenfeld (CH)

(72) Inventor: Frank Heuer, Filderstadt (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 0 days.

(21) Appl. No.: 15/560,331

(22) PCT Filed: Mar. 21, 2016

(86) PCT No.: PCT/EP2016/056167
§ 371 (c)(1),
(2) Date: Sep. 21, 2017

(87) PCT Pub. No.: WO2016/150920
PCT Pub. Date: Sep. 29, 2016

(65) Prior Publication Data
US 2018/0049781 A1    Feb. 22, 2018

(30) Foreign Application Priority Data
Mar. 24, 2015   (DE) .................. 10 2015 205 362

(51) Int. Cl.
*A61B 17/70*   (2006.01)
*A61B 17/16*   (2006.01)
*A61B 17/88*   (2006.01)

(52) U.S. Cl.
CPC ...... *A61B 17/7086* (2013.01); *A61B 17/7082* (2013.01); *A61B 17/7091* (2013.01);
(Continued)

(58) Field of Classification Search
CPC .................................. A61B 17/7074–17/7091
See application file for complete search history.

(56) References Cited

U.S. PATENT DOCUMENTS 9,861,419 B2 *   1/2018   Schafer .............. A61B 17/8875
2005/0149053 A1   7/2005   Varieur et al.
(Continued)

FOREIGN PATENT DOCUMENTS

DE   202011102890 U1 *  11/2011   ......... A61B 17/7086
DE   102013207183 A1    10/2014

OTHER PUBLICATIONS

Translation of DE202011102890U1.*
(Continued)

*Primary Examiner* — Lynnsy Summitt
(74) *Attorney, Agent, or Firm* — Bond Schoeneck & King, PLLC; George McGuire

(57) ABSTRACT

The invention relates to an instrument for connecting a correction rod to a bone screw, the instrument having an axial longitudinal direction and comprising an external first housing part, which includes a hollow portion having an internal thread and a portion that is approximately the shape of a half-shell and that forms a first clamp leg. The instrument further includes an external second housing part, which is approximately the shape of a half-shell and forms a second clamp leg that is hinged on the first clamp leg so as to be pivotable about a pivot axis that extends orthogonally to the axial longitudinal direction.

9 Claims, 6 Drawing Sheets

(52) U.S. Cl.
CPC ....... *A61B 17/1671* (2013.01); *A61B 17/7035* (2013.01); *A61B 17/8875* (2013.01)

(56) References Cited

U.S. PATENT DOCUMENTS

| | | | |
|---|---|---|---|
| 2005/0171540 A1* | 8/2005 | Lim | A61B 17/7005 606/86 A |
| 2006/0079909 A1* | 4/2006 | Runco | A61B 17/7076 606/99 |
| 2007/0093849 A1* | 4/2007 | Jones | A61B 17/7086 606/99 |
| 2007/0213716 A1* | 9/2007 | Lenke | A61B 17/025 606/264 |
| 2008/0015601 A1* | 1/2008 | Castro | A61B 17/7086 606/86 R |
| 2008/0234765 A1 | 9/2008 | Frasier | |
| 2010/0185248 A1 | 7/2010 | Barry et al. | |
| 2012/0277808 A1* | 11/2012 | May | A61B 17/7086 606/86 A |
| 2013/0018419 A1* | 1/2013 | Rezach | A61B 17/7076 606/264 |
| 2013/0066385 A1 | 3/2013 | Benoist | |
| 2014/0316423 A1* | 10/2014 | Schafer | A61B 17/8875 606/104 |

OTHER PUBLICATIONS

International Search Report Form PCT/ISA/210, International Application No. PCT/ EP2016/056167, pp. 1-3, International Filing Date Mar. 21, 2016, dated search report Jul. 18, 2016.

* cited by examiner

INSTRUMENT FOR CONNECTING A CORRECTION ROD TO A BONE SCREW

CROSS-REFERENCE TO RELATED APPLICATIONS

This application is the United States National Stage Application under 35 U.S.C. 371 of PCT/EP2016/056167 filed on Mar. 21, 2016, which claims priority German patent application No. 102015205362.8, filed on Mar. 24, 2015, the entire disclosure of each of which is incorporated herein by reference.

BACKGROUND OF THE INVENTION

The invention relates to an instrument for connecting a correction rod to a bone screw, in particular a pedicle screw in spinal surgery, said instrument having an axial longitudinal direction and comprising an external first housing part, which comprises a cylindrical hollow portion having an internal thread and a portion that is approximately the shape of a half-shell and that forms a first clamp leg, said instrument comprising an external second housing part, which is approximately the shape of a half-shell and forms a second clamp leg that is hinged on the first clamp leg so as to be pivotable in a limited manner about a pivot axis that extends orthogonally to the axial longitudinal direction, and said instrument comprising an adjustment part, which axially penetrates the external housing parts and is thus predominantly internal, and which comprises an external thread on one portion and can thus be screwed into the internal thread of the external first housing part, a proximal end of the adjustment part being manually graspable from outside the housing parts for this purpose, and said instrument comprising a rod pressure part, which can be axially placed against the correction rod and which is axially coupled to the adjustment part but can rotate about the axial longitudinal direction relative to the adjustment part, such that rotational movements of the adjustment part are not transmitted to the rod pressure part, and the clamp legs surrounding the rod pressure part in a shell-like manner and guiding same in a longitudinally slidable manner, said clamp legs each comprising a distal end and a proximal end, the relevant distal end engaging on the bone screw and the proximal end being actuatable by finger pressure of the operating surgeon.

An instrument of this kind is known from DE 10 2013 207 183 A1 by the applicant. In a previously known instrument of this kind, the first and second clamp legs each rest against a leg of an accommodation part, which is U-shaped when viewed from the side, of a pedicle screw when said pedicle screw is being gripped, such that the shell shapes of the clamp legs extend approximately concentrically to the legs of the U-shaped accommodation part in each case and provide between them the accommodation space, formed by the U shape, for a correction rod. The correction rod, or the longitudinal extension thereof, is therefore substantially parallel to the pivot axis of the joint of the two clamp legs of the instrument. However, this clamp joint requires a relatively large amount of installation space towards the pivot axis. As a result, the space next to the pedicle screw in question is limited in the direction of the longitudinal axis of the correction rod such that an adjacent pedicle screw cannot be readily gripped using another instrument at the same time.

The object of the present invention is to improve an instrument of the type mentioned with respect to the practical applicability thereof.

SUMMARY OF THE INVENTION

This object is achieved according to the invention in an instrument of the type mentioned in that the distal ends of the two clamp legs are designed such that they comprise an accommodation opening having a radial transverse direction for accommodating the correction rod in said radial transverse direction, and in that said radial transverse direction extends orthogonally to the pivot axis of the two clamp legs. In this way, an arrangement and/or orientation of the instrument and of a typically U-shaped accommodation part of the pedicle screw during use of the instrument during surgery are achieved according to the invention such that the longitudinal extension of the correction rod, or in the case of any bending of the correction rod the tangential extension thereof, extends in the region of the accommodation part of the pedicle screw approximately orthogonally to the pivot axis of the two clamp legs of the instrument. The protruding region of the pivot joint of the clamp legs therefore protrudes at the side transversely to the longitudinal direction or longitudinal extension of the correction rod, such that in this way space is saved next to the relevant pedicle screw in the longitudinal direction of the correction rod. Another very closely adjacent pedicle screw can thus be gripped using another corresponding instrument and secured to the correction rod. The invention is particularly advantageous in that more space is available in the rod direction than in previously known instruments. A plurality of instruments can be inserted along the rod at the same time in order to secure the correction rod and relevant pedicle screw. The solution according to the invention further implies that each leg of the U-shaped accommodation part of the pedicle screw is gripped by both clamp legs of the instrument in each case. The basic concept of the invention can also be described alternatively or additionally in this way.

The solution according to the invention could include suitable top pieces or end pieces on the two clamp legs. However, according to an embodiment of the invention, it is particularly advantageous if each of the distal ends of the two clamp legs comprises a slot that extends in the axial longitudinal direction, is continuous in the radial direction and opens out in unobstructed manner at the distal end face of the distal ends such that the correction rod can be inserted into said slot orthogonally to the longitudinal extension of said rod and in the axial longitudinal direction of the instrument. Each clamp leg therefore comprises two ribs between which the correction rod, which extends at least approximately in the radial transverse direction, is accommodated.

According to an embodiment of the invention, each clamp leg comprises two clamp fingers that extend in the axial longitudinal direction and are mutually spaced apart in the peripheral direction extending concentrically to the axial longitudinal direction. The relevant clamp fingers are preferably integral parts or regions of the clamp legs. The spacing is at least as big as the diameter of the correction rod and also extends in the axial longitudinal direction, such that the correction rod can be slidably accommodated therein.

In a development of the invention, it is advantageous if the two clamp fingers of a clamp leg comprise mutually facing projections in a distal end region and in the region of the spacing of said clamp fingers in the peripheral direction, which projections can be placed against different legs of a U-shaped accommodation part of the bone screw for the correction rod and thereby form an anti-rotation means between the bone screw and the instrument.

It is also advantageous if the clamp legs comprise ribs in a distal end region that extend radially inwardly concentrically and that can engage in concentrically extending grooves on the outer face of the legs of a U-shaped accommodation part of the bone screw in order to form a releasable positive coupling in the axial longitudinal direction between the bone screw and the instrument.

In another embodiment of the invention, which is however considered to be independently worthy of protection, it is advantageous if the rod pressure part enters into positive coupling with at least one clamp leg during increasing axial feed motion of the rod pressure part towards the bone screw and correction rod, such that an opening movement of the relevant clamp leg produced by pivoting about the pivot axis is prevented. In this way, it is ensured that when the axial pressure is at its greatest, i.e. when the correction rod and the pedicle screw are pressed against one another in the axial direction by means of the rod pressure part, the instrument cannot be released from the U-shaped accommodation part of the pedicle screw.

In a development of this concept of the invention, it is proposed for the rod pressure part to reach through radially outwards between the clamp fingers of at least one clamp leg by means of a radially projecting end piece and to engage around the clamp fingers during increasing axial feed motion of the rod pressure part towards the bone screw or the correction rod, and thus prevent an opening movement of the relevant clamp leg produced by pivoting about the pivot axis. For this purpose, it may be particularly advantageous if the radially projecting end piece of the rod pressure part is T-shaped or mushroom-shaped when viewed in a sectional plane orthogonal to the axial longitudinal direction. In this way, the radially projecting end piece can slide over the clamp fingers by means of the laterally protruding regions of the T or mushroom shape and thus prevent a pivoting of the clamp legs about the pivot axis.

According to another concept of the invention that is in itself independently worthy of protection, in a pivot joint for the two clamp legs, it is proposed for at least one joint pin to project radially inwards and for the inner end thereof to engage in a guide groove that extends in the axial longitudinal direction on the radial outer face of the rod pressure part and thus secures same against rotation but guides same in a longitudinally slidable manner in the longitudinal direction. In this way, it is possible for the rod pressure part to be non-rotatable relative to the housing parts in the shape of a half-shell, but also to be oriented and guided in a defined manner in the longitudinal direction with respect to the external first housing part of the instrument independently of the pivot position of the clamp legs.

In another embodiment of this concept of the invention, it is advantageous if the guide groove that extends in the axial longitudinal direction opens out at the radial outer face of the rod pressure part so as to widen in the manner of a V towards the distal end of the clamp legs. In this way, when the rod pressure part is inserted in the distal direction along the external first housing part, an independent centring takes place.

As already mentioned above, protection is further claimed for an instrument having the features of the preamble of claim 1, at least one clamp leg comprising two clamp fingers that extend in the axial longitudinal direction and that are mutually spaced apart in the peripheral direction extending concentrically to the axial longitudinal direction, and the rod pressure part reaching through radially outwards between the clamp fingers of the clamp leg by means of a radially projecting end piece and engaging around the clamp fingers during increasing axial feed motion of the rod pressure part towards the bone screw or the correction rod and thus preventing an opening movement of the relevant clamp finger produced by pivoting about the pivot axis. Preferably, this embodiment is implemented in both clamp legs or clamp shells in this manner.

Protection is further claimed for an instrument having the features of the preamble of claim 1, at least one joint pin in a pivot joint for the two clamp legs projecting radially inwards and the inner end thereof engaging in a guide groove that extends in the axial longitudinal direction on the radial outer face of the rod pressure part and thus secures same against rotation but guides same in a longitudinally slidable manner in the longitudinal direction. Preferably, this embodiment is implemented on both sides of the joint in this manner.

BRIEF DESCRIPTION OF THE DRAWINGS

Further features, details and advantages of the invention can be found in the accompanying claims and in the pictorial representation and following description of a preferred embodiment of the instrument according to the invention. In the drawings:

DETAILED DESCRIPTION

Figure 1:
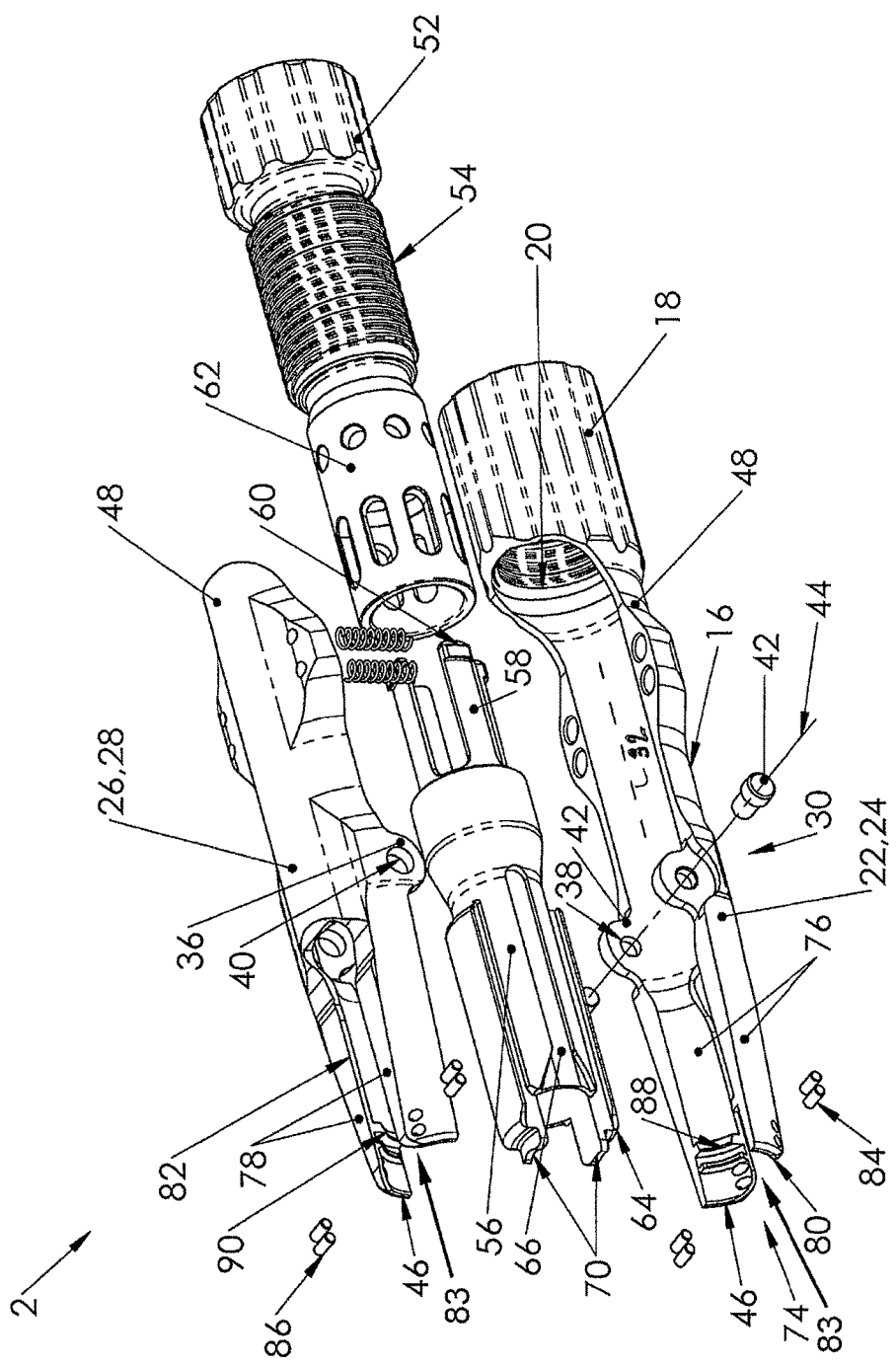
FIG. 1 is an exploded view of the instrument according to the invention.
Figure 3:
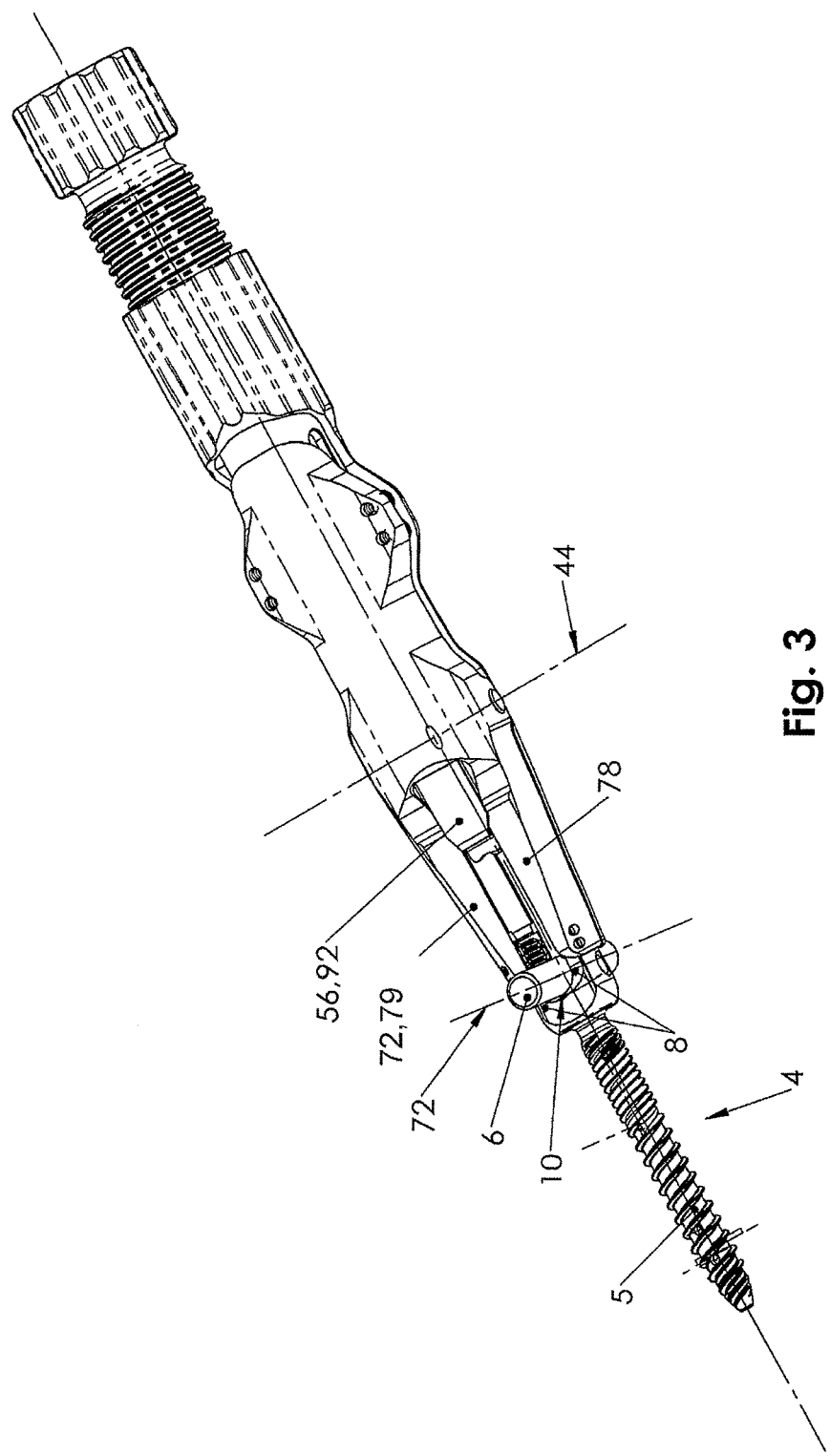
FIG. 3 is a perspective view of the instrument according to FIG. 1, the clamp legs of the instrument being secured on a bone screw and a correction rod being fitted in the U-shaped accommodation part of the bone screw, the rod pressure part not yet being adjacent.
Figure 4:
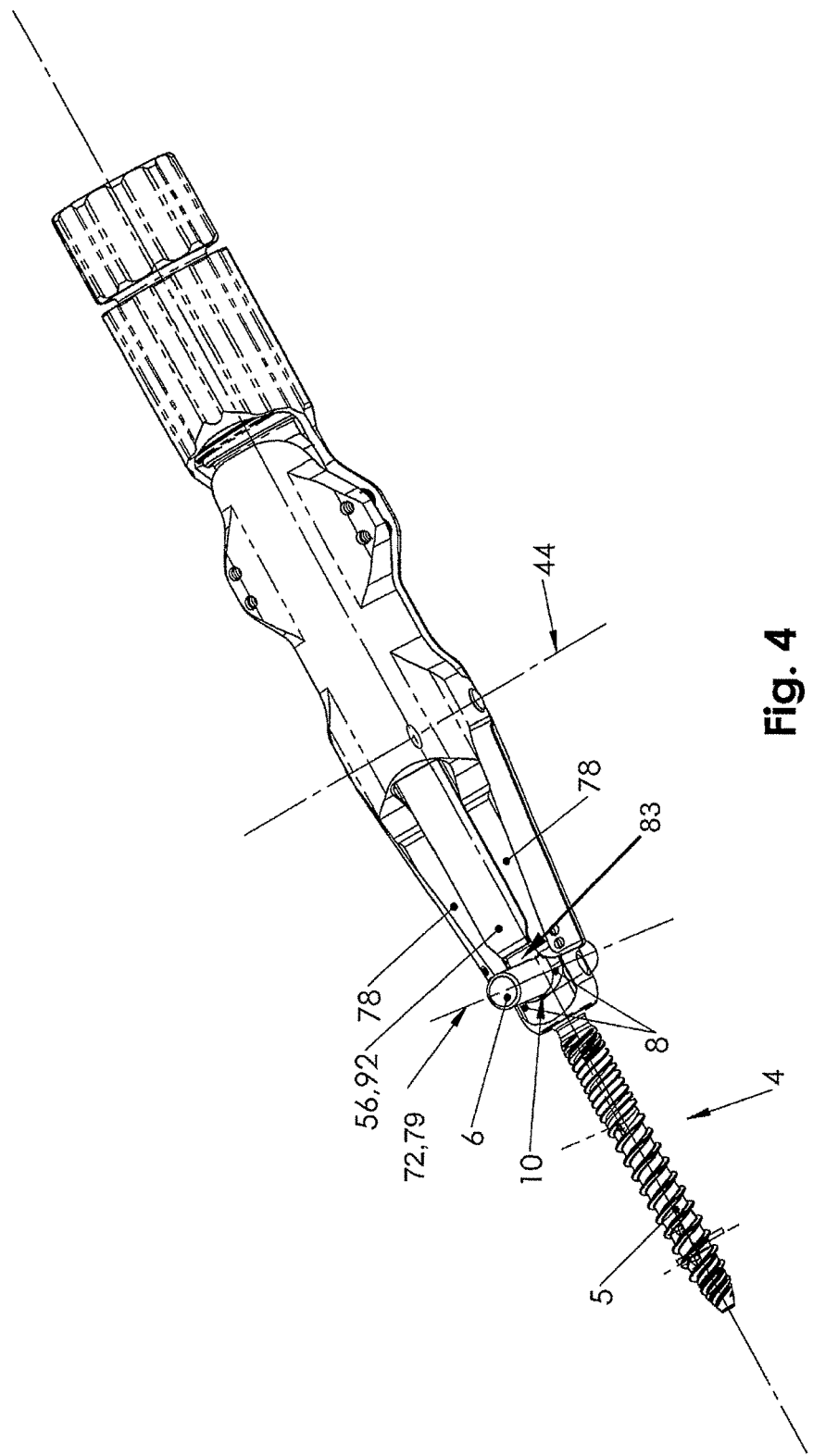
FIG. 4 is a perspective view of the instrument according to FIG. 3, the rod pressure part resting against the correction rod.

FIG. 1 shows, in exploded and perspective view, the essential components of an instrument generally denoted by the reference sign 2 and frequently referred to as a repositioning instrument. Said instrument is used to grip and hold a bone screw 4 comprising a threaded shaft 5, in particular a pedicle screw, and to correctly position a correction rod 6 on a bone screw 4 that has already been screwed into the bone. During the course of said positioning, the bone screw 4, as shown in FIGS. 3 and 4, is gripped, in a manner that will be described in greater detail, radially from the outside on the two legs 8 thereof of a U-shaped accommodation part 10 for the correction rod, the correction rod 6, in a manner that will also be described, being pressed against the U-shaped accommodation part 10 and fixed in an intended position by a screw means, in particular a set screw. This is done in a likewise known manner, in that the screw means is guided in the longitudinal direction through the internally hollow instrument 2 and screwed into the U-shaped accommodation portion 10 of the bone screw by means of a suitable instrument. The instrument 2 may also be used to grip and hold the bone screw 4 and to screw the threaded shaft 5 into the bone before the correction rod 6 is put in place, a tool application point on the proximal end of the threaded shaft 5 being accessed through the hollow instrument 2 by a tool, for the same purpose.

The instrument 2 comprises an external first housing part 16, which comprises a cylindrical, internally hollow portion 18 having an internal thread 20 and a portion 22 in the shape of a half-shell. This portion 22 in the shape of a half-shell forms a first clamp leg 24 of the instrument. Furthermore, the instrument comprises an external second housing part 26 that is approximately the shape of a half-shell and that forms a second clamp leg and is connected to the first clamp leg 24 via a pivot joint 30 so as to be pivotable in a limited manner. For this purpose, the first and second clamp legs 24 and 28 each comprise two joint tabs 34, 36, which extend towards one another and can be placed against one another, comprising aligned openings 38, 40 through which a threaded pin 42 extends in on both sides, which threaded pin hereby defines a pivot axis 44 of the two clamp legs 24, 28. A distal end 46 or a distal end region and a proximal end 48 or a proximal end region can also be seen on each of the clamp legs 24, 28. Pressure spring means 50 are arranged between the proximal end regions of the clamp legs 24, 28 such that they prestress the clamp legs 24, 28 about the pivot axis 44 such that the distal ends 46 thereof are forced against one another in order to be able to grip and hold a bone screw 4 by means of positive engagement. The second clamp leg 28 completes, to a certain extent, the external housing of the instrument 2 that has the approximate appearance of a hollow cylinder.

Furthermore, the instrument 2 comprises an internal adjustment part 52, which axially penetrates the housing parts 16, 26 described thus far and which can be screwed into the internal thread 20 of the cylindrical portion 18 of the first housing part 16 by means of an external thread 54, and a rod pressure part 56, which is coupled to the adjustment part 52 in the axial longitudinal direction 32 but can rotate about the axial longitudinal direction 32. For this purpose, the rod pressure part 56 comprises latching ribs 58 on the proximal end thereof that extend approximately in the axial longitudinal direction 32 and towards the adjustment portion 52, yield slightly transversely to the longitudinal direction 32 and each comprise a projection 60 that extends in the radial direction. The adjustment part 52 comprises an accommodation portion 62 that interacts herewith and comprises a corresponding peripheral groove (not shown) in which the projections 60 of the latching ribs 58 can engage when the two parts are axially joined. In this way, the parts are coupled in the axial longitudinal direction 32 and the rod pressure part 56 can rotate relative to the adjustment part 52.

Figure 2:
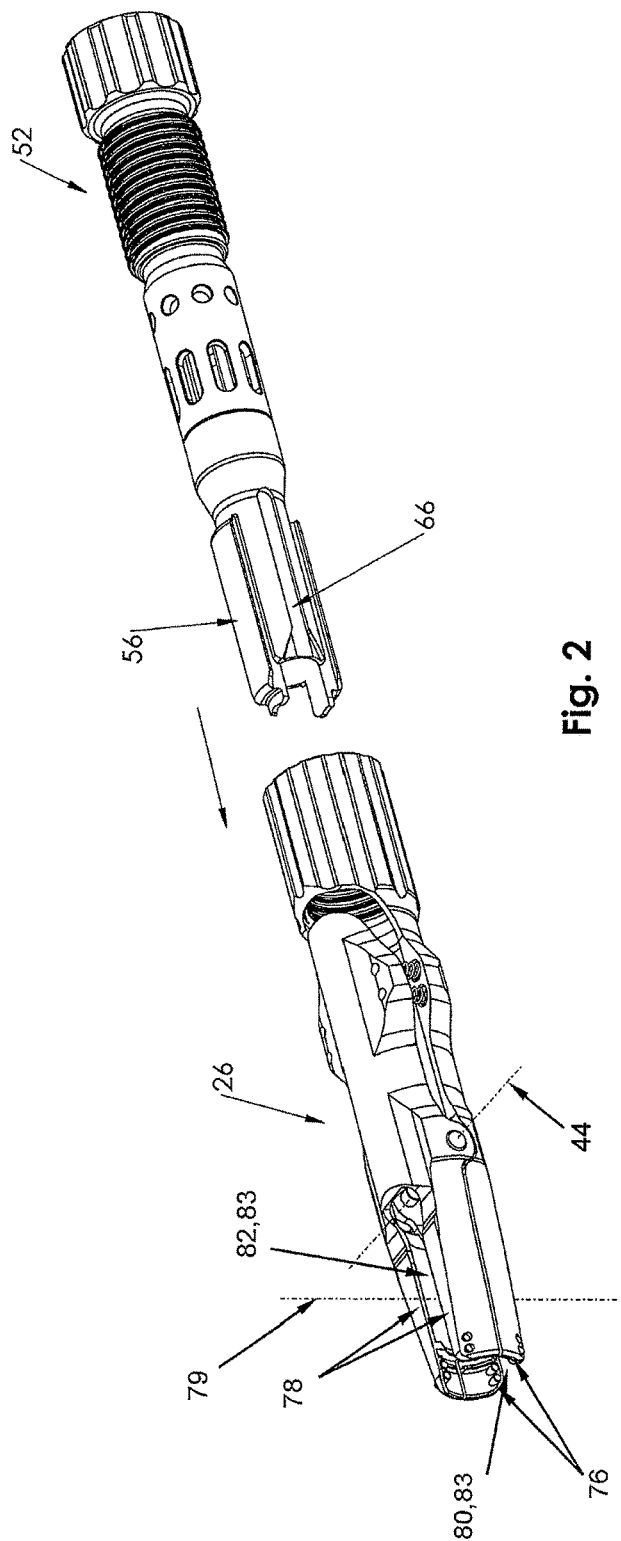
FIG. 2 is a perspective view of the external housing part, of the adjustment part that can be screwed therein and of the rod pressure part.

The rod pressure part 56 is likewise approximately hollow-cylindrical and comprises a guide groove 66 on the outer periphery 64 thereof on each diametrically opposed face, which guide groove extends in the axial longitudinal direction 32 and in which the free end of the two joint pins 42 engages. In this way, the rod pressure part 56 is accommodated in a longitudinally slidable yet non-rotatable manner in the two external housing parts 16, 26. The guide groove 66 is widened at the distal end in the manner of a V. This produces a centring aid for when the rod pressure part 56 and the adjustment part 52 coupled thereto are inserted into the housing in the axial longitudinal direction 32 (see FIG. 2). By means of the guide grooves 66 that widen in the manner of a V, the rod pressure part 56 readily reaches its correct position, in which the threaded pins 42 engage in the guide grooves 66 and hereby define the correct operating position of the rod pressure part relative to the housing parts 16, 26.

The rod pressure part 56 is further shifted in the distal direction by means of the adjustment part 52 being screwed into the internal thread 20 of the external first housing part 16. When the rod pressure part 56 is increasingly shifted in the distal direction, radially opposing end walls 70 on the distal end of the rod pressure part 56 ultimately come into axial abutment with the correction rod 6, whereas the clamp legs 24, 28 fixedly hold the pedicle screw in a manner yet to be described. By screwing the adjustment part 52 further in, the rod pressure part pushes the rod further towards the base of the U-shaped accommodation part 10 of the bone screw. Finally, as mentioned at the outset, the correction rod 6 is fixed against the accommodation part 10 by a screw means.

The external housing parts 16 and 26, or the clamp legs 24, 28 formed thereby, and the rod pressure part 56 are designed according to the invention such that the bone screw 4 or the U-shaped accommodation portion 10 thereof for the correction rod 6 are gripped and fixed in the gripped position such that a longitudinal extension or orientation 72 of the correction rod 6 extends orthogonally to the pivot axis 44 of the two clamps legs 24, 28. In this way, the pivot joint 30, which is relatively wide towards the pivot axis 44, is not arranged in the longitudinal direction of the rod, but rather transversely thereto. This saves space in the direction of the longitudinal extension 72 of the correction rod 6. As a result, a plurality of instruments can be inserted within a confined space at the same time in order to grip bone screws that are screwed in close to one another.

The two clamp legs 24, 28 that are approximately the shape of a half-shell are not continuous in the peripheral direction 74 extending concentrically to the axial longitudinal direction 32 in the region distal to the pivot axis 44, but rather each comprise two clamp fingers 76 and 78, respectively, which extend in the axial longitudinal direction 32. These clamp fingers 76, on one side, and 78, on the other side, are mutually spaced apart in the peripheral direction 74. Between said clamp fingers a slot 80 and 82, respectively, is formed which extends in the axial longitudinal direction 32 and is continuous in the radial transverse direction 79, and which forms an accommodation opening 83 for the correction rod 6. The width of said slot 80, 82 in the peripheral direction 74 is at least slightly greater than the diameter of the correction rod 6, such that said slot can accommodate said rod, even when said rod is slightly bent. The longitudinal extension 72 of the correction rod 6 thus extends exactly or, on account of slight bending, approximately in the radial direction 79 of the accommodation opening 83, which according to the invention extends orthogonally to the pivot axis 44 of the clamp legs 24, 28.

The clamp fingers 76 and 78, respectively, further comprise mutually facing, in particular pin-shaped projections 84, 86 in the region of the slot 80, 82, which engage around the U-shaped accommodation part 10 of the bone screw 6 such that they fix the legs 8 of the U-shaped accommodation part 10 in position in the peripheral direction 74, such that the U-shaped holding part 10 cannot rotate relative to the instrument 2. The axial coupling or securing is achieved by means of concentric annular ribs 88, 90 on the radially inner side of the clamp fingers 76 and 78, respectively, which engage in concentric grooves on the outer periphery of the legs 8 of the U-shaped holding part 10. When the bone screw 4 is gripped, each leg 8 of the U-shaped accommodation part 10 is thus contacted or gripped by both clamp legs 24, 28 on opposing sides. The longitudinal extension 72 of the rod 6 is therefore orthogonal to the pivot axis 44.

Figure 5:
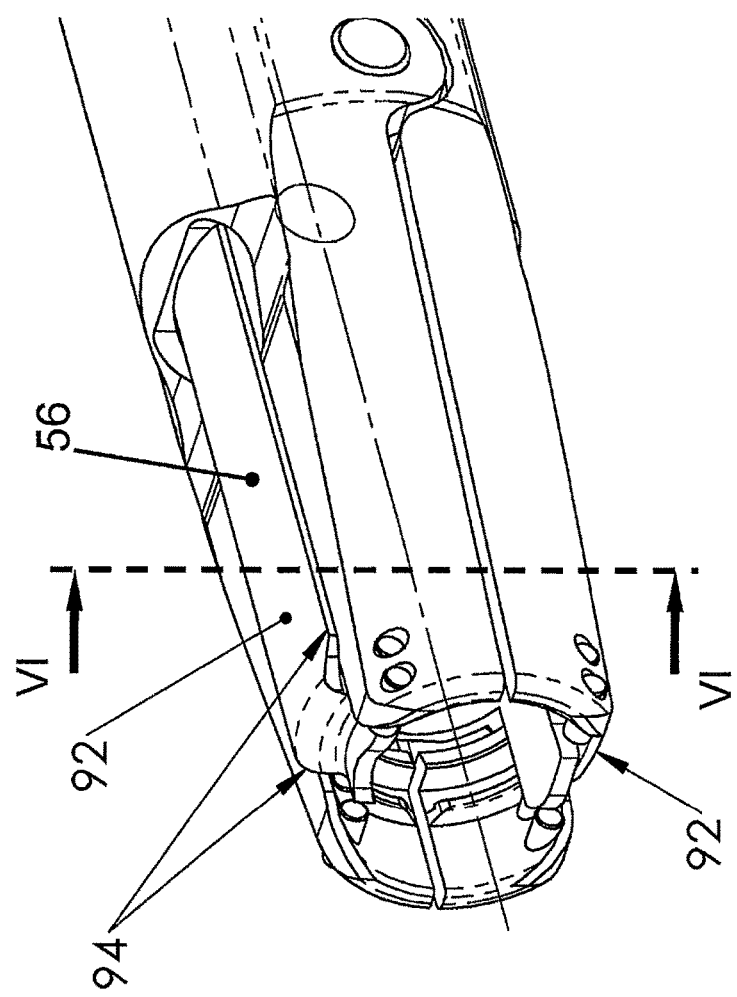
FIG. 5 is a perspective view of the distal end of the instrument.
Figure 6:
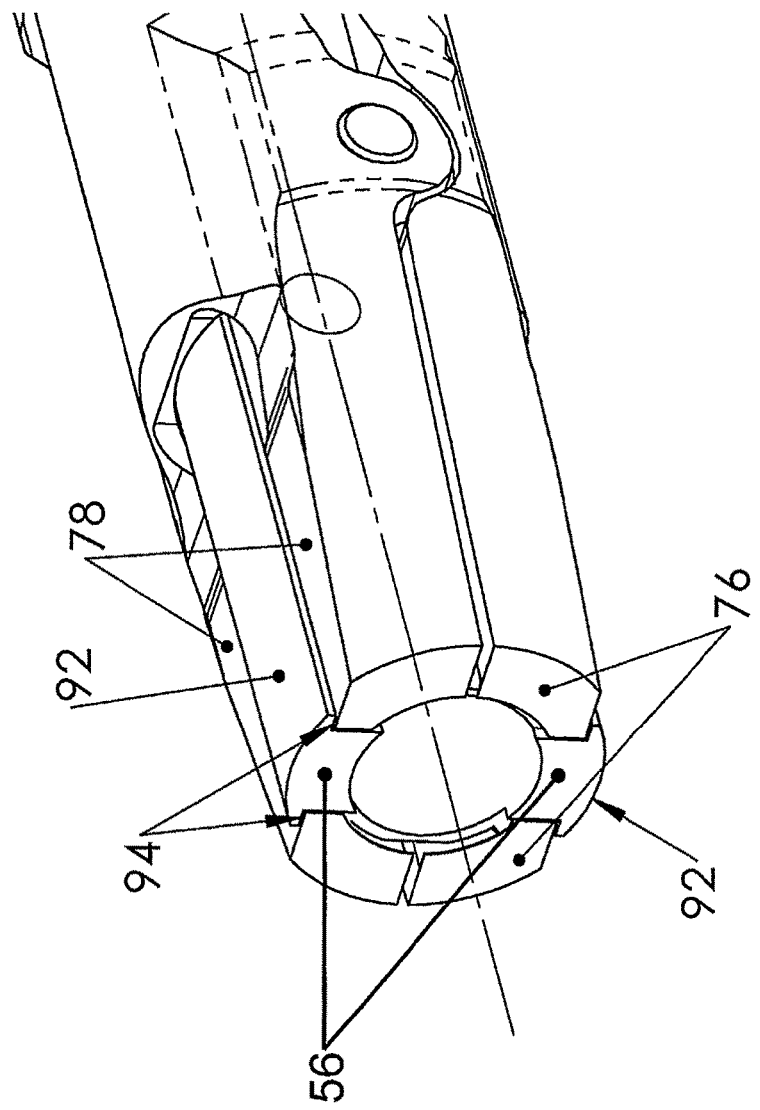
FIG. 6 is a perspective view corresponding to FIG. 5 cut along the sectional plane VI-VI from FIG. 5.

FIGS. 5 and 6 show another particularity of the instrument according to the invention. The rod pressure part 56 is designed and interacts with preferably both clamp legs 24, 28 such that an opening movement of the clamp legs produced by pivoting about the pivot axis 44 is prevented if the rod pressure part 56 has carried out a sufficient adjusting movement towards the distal end 46 of the clamp legs or the instrument. For this purpose, the rod pressure part 56 comprises a radially protruding end piece 92 on each diametrically opposed face. By means of this radial end piece 92, the rod pressure part 56 reaches outwards through the slot 80, 82 between the respective clamp fingers 76 and 78. The end piece 92 is in this case T-shaped or mushroom-shaped when viewed in the sectional plane from FIG. 6. Said end piece thus makes it possible to engage over the outer face of the clamp fingers 76 and 78 by means of the transversely extending legs 94 of the T or mushroom shape, namely in the region distal to the pivot axis 44, such that the clamp fingers 76, 78 and/or clamp legs 24, 28 can no longer open distally. In this way, the clamp legs are prevented from being able to unintentionally release from the rear engagement thereof on the outer face of the U-shaped accommodation portion of the pedicle screw when forces are introduced during operation of the instrument. In the case shown by way of example, the respective clamp fingers 76 and 78 are flattened in the contact region comprising the radial end piece 92, such that the transversely extending legs 94 of the T or mushroom shape and the clamp fingers 76 and 78 rest on one another in a planar manner such that the forces are distributed and evenly introduced such that material deformations are not produced by force peaks. In any case, by virtue of this embodiment, an absolutely secure axial anchoring of the instrument to the bone screw is achieved according to the invention at the time when force is introduced, i.e. when the bone screw or the U-shaped accommodation part 10 thereof and the correction rod 6 are drawn against one another. Only when the rod pressure part 56 releases the clamp fingers 76, 78 by means of the adjustment part 52 being unscrewed, in that said clamp fingers are brought out of engagement with the radial end piece 92, can the instrument be released from the bone screw once again. FIG. 3 approximately shows the region at which the radial end piece 92 of the rod pressure part 52 starts to engage over the clamp fingers 78 or releases said clamp fingers during the opposing return movement.

What is claimed is:

1. Instrument for connecting a correction rod to a bone screw, said instrument having an axial longitudinal direction and comprising an external first housing part, which comprises a cylindrical hollow portion having an internal thread and a portion that is approximately the shape of a half-shell and that forms a first clamp leg, said instrument comprising an external second housing part, which is approximately the shape of a half-shell and forms a second clamp leg that is hinged on the first clamp leg so as to be pivotable in a limited manner about a pivot axis that extends orthogonally to the axial longitudinal direction, and said instrument comprising an adjustment part, which axially penetrates the external housing parts and is thus internal, and which comprises an external thread on one portion and can thus be screwed into the internal thread of the external first housing part, a proximal end of the adjustment part being manually graspable from outside the housing parts for this purpose, and said instrument comprising a rod pressure part, which can be axially placed against the correction rod and which is axially coupled to the adjustment part but can rotate about the axial longitudinal direction relative to the adjustment part, such that rotational movements of the adjustment part are not transmitted to the rod pressure part, and the clamp legs surrounding the rod pressure part in a shell-like manner and guiding same in a longitudinally slidable manner, said clamp legs each comprising a distal end and a proximal end, the relevant distal end engaging on the bone screw and the proximal end being actuatable by finger pressure of the operating surgeon, characterized in that the distal ends of the two clamp legs are designed such that they comprise an accommodation opening having a radial transverse direction for accommodating the correction rod in said radial transverse direction, and in that said radial transverse direction extends orthogonally to the pivot axis of the clamp legs, further characterized in that, in a pivot joint for the two clamp legs, at least one joint pin projects radially inwards and the inner end thereof engages in a guide groove that extends in the axial longitudinal direction on a radial outer face of the rod pressure part and thus secures same against rotation but guides same in a longitudinally slidable manner in the longitudinal direction.

2. Instrument according to claim 1, characterized in that each of the distal ends of the two clamp legs comprises a slot that extends in the axial longitudinal direction, is continuous in the radial direction and opens out in unobstructed manner at the distal end face of the distal ends such that the correction rod can be inserted into said slot orthogonally to the longitudinal extension of said rod and in the axial longitudinal direction of the instrument.

3. Instrument according to claim 1, characterized in that each clamp leg comprises two clamp fingers that extend in the axial longitudinal direction and are mutually spaced apart in the peripheral direction extending concentrically to the axial longitudinal direction.

4. Instrument according to claim 3, characterized in that the two clamp fingers of a clamp leg comprise mutually facing projections in a distal end region and in the region of the spacing of said clamp fingers in the peripheral direction, which projections can be placed against different legs of a U-shaped accommodation part of the bone screw for the correction rod and thereby form an anti-rotation means between the bone screw and the instrument.

5. Instrument according to claim 3, characterized in that the rod pressure part enters into positive coupling with at least one clamp leg during increasing axial feed motion of the rod pressure part towards the bone screw or correction rod, such that an opening movement of the relevant clamp leg produced by pivoting about the pivot axis is prevented.

6. Instrument according to claim 5, characterized in that the rod pressure part reaches through radially outwards between the clamp fingers of at least one clamp leg by means of a radially projecting end piece and engages around the clamp fingers during increasing axial feed motion of the rod pressure part towards the bone screw and correction rod, and thus prevents an opening movement of the relevant clamp leg produced by pivoting about the pivot axis.

7. Instrument according to claim 6, characterized in that the radially projecting end piece of the rod pressure part is T-shaped or mushroom-shaped when viewed in a sectional plane orthogonal to the axial longitudinal direction.

8. Instrument according to claim 1, characterized in that the clamp legs comprise ribs in a distal end region that extend radially inwardly concentrically and that can engage in concentrically extending grooves on the outer face of the legs of a U-shaped accommodation part of the bone screw in order to form a releasable positive coupling in the axial longitudinal direction between the bone screw and the instrument.

9. Instrument according to claim 1, characterized in that the guide groove that extends in the axial longitudinal direction opens out at the radial outer face of the rod pressure part so as to widen in the manner of a V towards the distal end of the clamp legs.

* * * * *